United States Patent [19]

Gruber et al.

[11] 4,330,620
[45] May 18, 1982

[54] METHOD AND REAGENT FOR THE DETERMINATION OF CREATINE KINASE MB

[75] Inventors: Wolfgang Gruber, Tutzing-Unterzeismering; Helmut Lenz, Tutzing; Siegfried Looser, Weilheim; Hans-Ralf Linke, Raisting, all of Fed. Rep. of Germany

[73] Assignee: Boehringer Mannheim GmbH, Mannheim-Waldhof, Fed. Rep. of Germany

[21] Appl. No.: 125,318

[22] Filed: Feb. 28, 1980

[30] Foreign Application Priority Data

Mar. 2, 1979 [DE] Fed. Rep. of Germany ....... 2908053

[51] Int. Cl.$^3$ ...................... G01N 33/54; C12Q 1/50; C12N 9/99
[52] U.S. Cl. ............................ 435/7; 435/8; 435/17; 435/184
[58] Field of Search ....................... 435/4, 7, 8, 17, 69, 435/810, 272, 262, 267, 184; 23/230 B; 424/12, 85; 260/112 R

[56] References Cited

U.S. PATENT DOCUMENTS

| | | | |
|---|---|---|---|
| 3,932,221 | 1/1976 | Pfleider | 435/17 |
| 4,001,088 | 1/1977 | Antonik | 435/8 |
| 4,067,775 | 1/1978 | Wurzburg et al. | 435/184 |
| 4,200,436 | 4/1980 | Mochida | 424/12 |

OTHER PUBLICATIONS

Gerhardt et al, "Creatine Kinase B-subunit Activity in Serum After Immunoinbition of M-subunit Activity", *Chem. Absts.*, vol. 91, No. 11, p. 312 (1979) abs. No. 86102y.

Malakhov, "Interaction of Human Creatine Phosphokinase Isoenzymes With Rabbit Antibodies and Their Fab-fragments", *Chem. Absts.*, vol. 90, No. 13 p. 416, (1979) abs. No. 101737j.

Wuerzburg, et al, "Determination of Creatine Kinase MB Activity", *Chem. Absts.*, vol. 87, No. 7, p. 161, (1977), abs. No. 49467t.

Jockers-Wretou et al, "Quantitation of Creatine Kinase Isoenzymes in Human Tissues and Sera by an Immunological Method", *Clin. Chim. Acta*, vol. 58, No. 3, (1975) pp. 223-232.

Gerhardt, et al. "Creatine Kinase B-subunit Activity in Human Serum I", *Clin. Chim. Acta.*, vol. 78, No. 1, (1977), pp. 29-41.

*Primary Examiner*—Thomas G. Wiseman
*Attorney, Agent, or Firm*—Felfe & Lynch

[57] ABSTRACT

A method for the determination of creatine kinase-MB in serum by immunological exclusion of sub-unit M and measurement of the sub-unit B for the determination of creatine kinase, the improvement comprising, for the purpose of excluding the sub-unit M, adding to the reaction mixture comprising determination reagents and the creatine kinase-containing sample, monovalent fragments obtained from antibodies against the sub-unit M by proteolytic cleavage under reducing conditions.

14 Claims, No Drawings

METHOD AND REAGENT FOR THE DETERMINATION OF CREATINE KINASE MB

The invention relates to a method and a reagent for determining the activity of creatine phosphokinase MB, hereinafter referred to as "CK-MB", in serum.

BACKGROUND

In the human body, two different types of sub-units occur in this enzyme, namely sub-units M and B. Since the active enzyme is composed of two sub-units, and since the two sub-units can combine freely with one another, three types of enzyme are possible: the muscle type CK-MM, the brain type CK-BB and the hybrid type CK-MB, which occurs mainly in the myocardium, passes into the serum in myocardial infarction, and can then be found in the serum in an elevated concentration. The activity of this hybrid isoenzyme, in addition to the total activity of the CK in the serum, can be used in the diagnosis of myocardial infarction.

It is known to add specific antibodies against the M sub-unit of CK so as to exclude the muscle type CK-MM of the isoenzyme, and then to measure the remaining hybrid enzyme CK-MB by any of the known methods for the determination of CK, using either precipitating or inhibiting antibodies. One disadvantage, however, is that in this case the hybrid enzyme CK-MB is 80% inhibited (Clin. Chim. Acta, 58, 223–232 (1975)). It was already known to obtain antibodies which completely inhibit the muscle type CK-MM, but which do not at all inhibit the brain type CK-BB (Immunochemistry, Vol. 6, 681–687 (1969)). Although in such antibodies the sub-unit B in the hybrid enzyme CK-MB is not at all inhibited and therefore the reliability of the method of determination is thereby increased, this method also has considerable disadvantages. For it has been found that, even when high-purity antigens (CK-MM) are used, the animals used for the formation of the antibody mostly supplied a serum which effected a more than 55% inhibition, usually between 60 and 90%, of the hybrid enzyme CK-MB. Therefore, it was necessary, for each individual animal used for the immunization, to find out whether the antibody that had been formed inhibited the CK-MB to only 50%, or inhibited it more strongly. Aside from the expense and difficulty this involved, it was found that most of the serums obtained were virtually unusable, since different degrees of inhibition always occurred. Even pooled sera are only a partial remedy for this difficulty. In addition, the amount of CK-MB in the serum in myocardial infarction is extremely small, and in the case of antibodies which exclude any appreciable additional amount thereof, the reliability of the method is greatly reduced.

THE INVENTION

The invention is addressed to the object of eliminating these disadvantages and of creating a method of the kind described which will make it possible to use even antibodies which completely inhibit CK-MM but inhibit CK-MB to more than 55%, such that the total activity of the sub-unit B contained in the hybrid enzyme CK-MB can be determined.

This object is accomplished in accordance with the invention by a method for the determination of creatine kinase-MB in the serum by immunological exclusion of sub-unit M and measurement of the sub-unit B by known methods for the determination of creatine kinase, which is characterized by adding monovalent fragments obtained by proteolytic cleavage under reducing conditions from antibodies against sub-unit M for the purpose of excluding the sub-unit M in the reaction mixture.

It is known that enzymes are inhibited not only by the natural antibodies which belong to the IgG fraction and to the gamma globulins and which have a molecular weight of about 130,000 to 210,000, but also that the proteolytic cleavage of these antibodies results in fragments which have lost their ability to precipitate, since they are then no more than monovalent, in contrast to the bivalent antibodies, but that nevertheless the inhibiting properties of the monovalent fragments are only slightly different from those of the bivalent antibodies (Kontakte 3/78, U. Würzburg, Analyse von Enzymsystemen mit hemmenden Antikörpern, pages 10–17). Such monovalent fragments are referred to as FAB fragments (Biochem. J. 73, 119–126 (1959); Immunochem. 4, 369 (1967)).

Surprisingly it has been found that, in the present case, this is not true, and that, from antibodies which completely inhibit CK-MM and inhibit CK-MB to more than 55%, especially to 60 to 90%, monovalent fragments (FAB-fragments) are obtained, which still completely, i.e., to 99 to 100%, inhibit CK-MM, but inhibit CK-MB to only 50% within the margin of error. Thus it becomes possible to use for the determination of CK-MB antisera obtained from suitable experimental animals, such as sheep, guinea pigs, chickens and the like, without first having to apply complex analytical methods for the segregation of those antisera which inhibit CK-MB to more than about 53%. Instead, it is now possible to cleave the sera proteolytically under reducing conditions, without previously determining their inhibiting properties, and then to use the cleavage fragments to specifically exclude the sub-unit M of the CK, whether it is present in the muscle enzyme CK-MM or in the hybrid enzyme CK-MB. It is preferred in the scope of the invention to use monovalent fragments which are obtained from antibodies which inhibit the hybrid enzyme CK-MB to more than 55%, and especially to 60 to 90%, and which completely inhibit the muscle-type isoenzyme CK-MM.

According to an additional, preferred embodiment of the invention, those monovalent fragments are used from which the rest of the complete antibodies and the crystallizable fragments ($F_c$) have been separated. The separation can be accomplished by known methods such as, for example, gel chromatography, or dialysis against salt solution and precipitation with zinc sulfate (Immunochem. 14, 99 (1977).

The monovalent fragments obtained in a known manner, which, as stated, have preferably been purified of antibodies and $F_c$ fragments, can be used directly in the method of the invention. It is preferable that monovalent fragments are used whose SH groups have been alkylated. Those alkylating agents are suitable which are active in an aqueous medium at pH values which do not alter the tertiary structure of proteins. Examples are iodine acetate and iodine acetamide, the latter being used preferentially, since it is simultaneously capable of inactivating the proteolytic enzymes used in preparing the fragments.

In the preparation of the antisera required for the production of the FAB fragments used in accordance with the invention, conventional immunization methods are applied, such as have often been described in the literature. See, for example, "Methods of Immunology and Immunochemistry", vol. 4, 313 ff (1976), especially p. 336. Generally it is important in immunization to use very pure antigens and to immunize for a sufficiently long period of time. The general methods are described, for example, in "Immunologische Arbeitsmethoden", VEB Gustav Fischer Verlag, Jena, 1976, 368–370, and "Microbiology", Harper & Row, New York, 1970, 458–459. Pure CK-MM isoenzymes (antigens) suitable for the immunization can be obtained in accordance with ABB 150, 648–678 (1972), it being desirable to add dithiothreitol to the buffer for stabilization during the isolation and purification.

The IgG fraction and gamma globulin are obtained from the antisera in the conventional manner, and they are then cleaved under reducing conditions with a proteolytic enzyme which attacks the hinge region. Examples of such enzymes are papain and pepsin. The cleavage is described, for example, in "The Antibody Molecule", Academic Press, New York, 1975, 322–326. To establish the reducing conditions, compounds which contain SH groups are added, as a rule, such as cysteine, mercaptoethanol and the like. The incubation with the proteolytic enzyme is stopped when the cleavage is complete, by adding, for example, one of the known inactivating agents. As stated above, iodine acetamide is preferred in the scope of the invention. The free SH groups of the FAB fragments, which have been produced by the cleavage, are alkylated by this inactivating agent. FAB fragments treated in this manner are especially suitable in the scope of the invention, especially if all remaining antibodies and $F_c$ fragments are removed. The inhibition of the CK-MB then takes place completely without the occurrence of precipitates, and amounts virtually precisely to 50%. However, in the scope of the invention those FAB fragments can also be used which are not alkylated or have not been purified of accompanying substances, even though there is a slightly greater error in the determination, but one that is still within the margin of usefulness, i.e., FAB fragments which inhibit the hybrid enzyme to 50%±3%.

The determination of sub-unit B in the CK-MB hybrid enzyme after the addition of the monovalent antibody is then accomplished by the methods generally known for the determination of CK, which set out from creatine or from creatine phosphate. Suitable methods are described, for example, in "Methoden der enzymatischen Analyse" by H. U. Bergmeyer, Verlag Chemie, Vol. 1, 3rd edition, pp 813–825. A method which is particularly suitable on account of its great sensitivity is described, for example, in German Patent Application No. P2908053 (now DE-OS 290853) (filed Mar. 2, 1979, under int. No. 2292 of the same applicant). This method uses the luciferinluciferase reaction and kinetically measures the amount of light that is emitted.

The method of the invention makes possible the quantitative determination of CK-MB by the use of antisera against CK-MM which are obtained by any of the immunization methods described in the literature and which heretofore have not been usable for a diagnostically reliable CK-MB test due to the excessively high inhibition of CK-MB. Antisera which cause precipitation in addition to inhibition can also be used in accordance with the invention. Antisera with excessive CK-MB inhibition, which are produced to a very considerable extent even in refined immunization methods, no longer have to be segregated, and the complex analysis formerly needed in order to differentiate between usable and non-usable antisera is no longer necessary. This is particularly important, because the testing of the CK-MB inhibition of an antiserum can be accomplished only with CK-MB preparations from fresh serum from myocardial infarction patients. The elimination of the inhibition test therefore results in a considerable simplification.

EXAMPLES

The following examples will further explain the invention.

EXAMPLE 1

(a) Preparation of the IgG fraction

Serum from sheep immunized with human CK-MM by the method described in "Immunologische Arbeitsmethoden", *loc. cit.*, is treated with 1.8 M of crystalline ammonium sulfate at 0° to 4° C. and pH 7. After centrifugation, the precipitate is dissolved in 0.1 M of TRIS mixed with 0.15 M of sodium chloride buffer, pH 8, and is thoroughly dialyzed against 10 mM of phosphate buffer, pH 7.1. The dialyzate, repeatedly clarified by centrifugation, is placed on a column that is filled with DEAE cellulose. The proteinic liquid that passes through the column and the eluate that is obtained from the column with 15 mM of phosphate mixed with 10 mM of NaCl buffer, pH 7.1, are combined, and they contain more than 95% pure IgG.

(b) Papain cleavage

IgG is incubated with 1.5% of papain by weight (with respect to the amount of IgG protein) under reducing conditions (10 mM of cysteine) in the method described in Immunochem. 4 (1967) 369, at pH 7.5 for 5 hours at 37° C. At the end of the incubation phase, the enzyme action is stopped with an excess of iodine acetamide and the mixture is incubated at pH 7.5 for 2 hours at room temperature to alkylate the free SH groups. The stabilized cleavage mixture contains FAB fragments, $F_c$ fragments and less than 10% of uncleaved IgG. The immune reactivity yield amounts to more than 75%.

(c) Purification of the FAB fragments

After concentration to 30 mg/ml by ultrafiltration, the cleavage mixture is analyzed by gel chromatography (The LKB Instrument Journal 24, (1977) 10). FAB fragments elute as the first protein peak, well separated from IgG and $F_c$ fragments. The FAB fraction can be used directly, after concentration by ultrafiltration, for the inhibition of CK-MM or CH-MB. The inhibition of CK-MB amounts to 50% within the margin of error. The inhibition of CK-MM is 99 to 100%.

EXAMPLE 2

(a) Preparation of the gamma globulin fraction from sheep plasma.

Citrate plasma from sheep immunized for 4 to 6 months with CK-MM is treated with 25 mM of calcium chloride and allowed to coagulate for 2 hours at room temperature. The coagulum is broken up mechanically and diluted with one volume of physiological NaCl solution, and treated with 2% of silicate flocculant (aerosil) for the adsorption of lipo-protein. The clear supernatant liquid is obtained by centrifugation. From this the gamma globulin fraction is precipitated at 0° to 4° C. and pH 7 with 1.8 M of ammonium sulfate, and collected by centrifugation. By dialysis against 50 mM of TRIS mixed with 0.1 M of sodium chloride buffer, pH 7.5, and concentration by ultrafiltration, an antibody preparation suitable for enzymatic cleavage is obtained.

(b) Papain cleavage.

The method described in Example 1 b) is followed, but it is slightly modified for the gamma globulin fraction. 1.5% of papain, with respect to the grams of protein of the gamma globulin fraction, is used, and the incubation time amounts to 20 hours at 25° C. The rest of the conditions are the same.

(c) Purification of the FAB fraction.

The alkylated cleavage mixture is dialyzed against physiological salt solution, and then 25 mM of zinc sulfate is added (Immunochem. 14 (1977) 99). This precipitates any uncleaved IgG and $F_c$ fragments, which are then separated by centrifugation. The remaining FAB fragments, after dialysis and concentration, are ready for use in the CK-MB test. The yield amounts to more than 80% of the inhibiting activity for CK-MM isoenzyme, with respect to the starting plasma. CK-MB is 50% inhibited regardless of the inhibition rate for the uncleaved antibodies. The results obtained with various sera are shown in the following table.

TABLE

| | % of Inhibition of Enzyme Activity | | | |
|---|---|---|---|---|
| | CK-MM (600–1000 U/l) | | CK-MB (200–400 U/l) | |
| Animal No. | Starting serum | FAB fragments | Starting serum | FAB fragments |
| 1 | 99.5 | 99.5 | 62 | 52 |
| 2 | 99.6 | 99.7 | 56 | 53 |
| 3 | 99.3 | 99.1 | 64 | 49 |
| 4 | 98.5 | 99.3 | 68 | 52 |

It will be understood that the specification and examples are illustrative but not limitative of the present invention and that other embodiments within the spirit and scope of the invention will suggest themselves to those skilled in the art.

What is claimed is:

1. In a method for the determination of creatine kinase-MB in serum sample of the type comprising immunologically neutralizing the sub-unit M in the sample with an antibody, and then measuring for the enzymatic activity of the sub-unit B of creatine kinase, the improvement comprising neutralizing the sub-unit M with monovalent antibody fragments prepared by proteolytic cleavage under reducing conditions of antibodies which completely inhibit the isoenzyme CK-MM.

2. The method as claimed in claim 1 wherein said monovalent fragments are obtained from antibodies which inhibit the hybrid enzyme CK-MB to more than 55% and completely inhibit the isoenzyme CK-MM.

3. The method as claimed in claim 2 wherein the monovalent fragments are obtained from antibodies which inhibit the hybrid enzyme CK-MB to from 60 to 90%.

4. The method as claimed in claim 1 wherein, from said monovalent fragments, the residual complete antibodies and the crystalline fragments $F_c$ have been separated.

5. The method as claimed in claim 1 wherein in said monovalent fragments the SH groups are alkylated.

6. The method as claimed in claim 5 wherein said monovalent fragments are alkylated with iodine acetamine or iodine acetate.

7. The method as claimed in claim 1 wherein the sub-unit B is determined by the luciferin-luciferase reaction and the emitted amount of light is measured kinetically.

8. In a reagent for the determination of creatine kinase MB comprising a reagent system for the enzymatic determination of creatine kinase MB and means for the immunological neutralization of sub-unit M of the creatine kinase MB wherein the improvement comprises using as the means a monovalent antibody fragments prepared by proteolytic cleavage under reducing conditions of antibodies which completely inhibit isoenzyme CK-MM.

9. The reagent as claimed in claim 8 wherein said monovalent fragments are obtained from antibodies which inhibit the hybrid enzyme CK-MB to more than 55% and completely inhibit the isoenzyme CK-MM.

10. The reagent as claimed in claim 9 wherein the monovalent fragments are obtained from antibodies which inhibit the hybrid enzyme CK-MB to from 60 to 90%.

11. The reagent as claimed in claim 8 wherein, from said monovalent fragments, the residual complete antibodies and the crystalline fragments $F_c$ have been separated.

12. The reagent as claimed in claim 8 wherein, in said monovalent fragments, the SH groups are alkylated.

13. The reagent as claimed in claim 12 wherein said monovalent fragments are alkylated with iodine acetamine or iodine acetate.

14. The reagent as claimed in claim 8 wherein said system for the determination of creatine kinase-MB is the luciferin-luciferase system providing for kinetic measurement of the emitted amount of light.

* * * * *